(12) United States Patent
Hansen et al.

(10) Patent No.: US 8,076,618 B2
(45) Date of Patent: Dec. 13, 2011

(54) MODULAR FLUID WARMER

(75) Inventors: William J. Hansen, Pewaukee, WI (US); Terence T. Smith, Waukesha, WI (US)

(73) Assignee: Enthermics Medical Systems, Inc., Menomonee Falls, WI (US)

( * ) Notice: Subject to any disclaimer, the term of this patent is extended or adjusted under 35 U.S.C. 154(b) by 678 days.

(21) Appl. No.: 12/208,166

(22) Filed: Sep. 10, 2008

(65) Prior Publication Data

US 2010/0059498 A1 Mar. 11, 2010

(51) Int. Cl.
*A61M 5/44* (2006.01)
*A61F 7/00* (2006.01)
*A61B 19/00* (2006.01)
*H05B 3/22* (2006.01)
*H05B 3/66* (2006.01)

(52) U.S. Cl. .......................... 219/428; 219/386; 604/114

(58) Field of Classification Search ........................ None
See application file for complete search history.

(56) References Cited

U.S. PATENT DOCUMENTS

| | | | | |
|---|---|---|---|---|
| 3,606,949 | A | * | 9/1971 | Joyce .......................... 211/126.5 |
| 3,791,528 | A | * | 2/1974 | Brendgord .................. 211/88.01 |
| 3,860,309 | A | * | 1/1975 | Brendgord .................... 312/351 |
| 5,408,576 | A | | 4/1995 | Bishop |
| 5,733,263 | A | | 3/1998 | Wheatman |
| 5,986,239 | A | * | 11/1999 | Corrigan et al. .............. 219/385 |
| 6,142,974 | A | | 11/2000 | Kistner et al. |
| 6,259,067 | B1 | | 7/2001 | Faries et al. |
| 6,294,762 | B1 | | 9/2001 | Faries et al. |
| 6,376,805 | B2 | | 4/2002 | Faries et al. |
| 6,384,380 | B1 | | 5/2002 | Faries et al. |
| 6,467,953 | B1 | | 10/2002 | Faries et al. |
| 6,566,631 | B2 | | 5/2003 | Faries et al. |
| 6,660,974 | B2 | | 12/2003 | Faries et al. |
| 6,768,085 | B2 | | 7/2004 | Faries et al. |
| 6,869,538 | B2 | | 3/2005 | Yu et al. |
| 7,010,221 | B2 | | 3/2006 | Augustine et al. |
| RE39,075 | E | | 4/2006 | Verkaart |
| 7,031,602 | B2 | | 4/2006 | Faries et al. |
| 7,041,941 | B2 | | 5/2006 | Faries et al. |
| 7,128,275 | B2 | | 10/2006 | Kammer et al. |
| 7,153,285 | B2 | | 12/2006 | Lauman et al. |
| 7,158,719 | B2 | | 1/2007 | Cassidy |
| 7,238,170 | B2 | | 7/2007 | Park |
| 7,238,171 | B2 | | 7/2007 | Faries et al. |
| 7,276,675 | B2 | | 10/2007 | Faries et al. |
| 7,307,245 | B2 | | 12/2007 | Faries et al. |
| 7,326,882 | B2 | | 2/2008 | Faries et al. |
| 7,441,714 | B2 | | 10/2008 | Kammer et al. |
| 7,459,657 | B2 | | 12/2008 | Kammer et al. |
| 2001/0042743 | A1 | | 11/2001 | Faries et al. |
| 2002/0021741 | A1 | | 2/2002 | Faries et al. |

(Continued)

OTHER PUBLICATIONS

PCT International Search Report for PCT/US2009/056464, mailed Feb. 4, 2010. (2 pages).

*Primary Examiner* — Joseph M Pelham
(74) *Attorney, Agent, or Firm* — Quarles & Brady LLP

(57) ABSTRACT

The present invention provides a modular fluid warmer and a method of stacking a plurality of modular fluid warmers. As each of the modular fluid warmers is independently operated, the modular fluid warmers are energy efficient. Further, each modular fluid warmer may be equipped with sensors and a controller that reduces the required amount of user interaction with the modular fluid warmer.

20 Claims, 13 Drawing Sheets

U.S. PATENT DOCUMENTS

| | | |
|---|---|---|
| 2002/0158058 A1 | 10/2002 | Faries et al. |
| 2003/0000939 A1 | 1/2003 | Faries et al. |
| 2004/0188409 A1 | 9/2004 | Faries et al. |
| 2004/0247016 A1 | 12/2004 | Faries et al. |
| 2006/0086361 A1 | 4/2006 | Kammer et al. |
| 2006/0289016 A1 | 12/2006 | Kammer et al. |
| 2006/0291533 A1 | 12/2006 | Faries et al. |
| 2007/0000910 A1 | 1/2007 | Faries et al. |
| 2007/0015975 A1 | 1/2007 | Faries et al. |
| 2007/0088249 A1* | 4/2007 | Duffy et al. ............ 604/65 |
| 2008/0152937 A1 | 6/2008 | Kammer et al. |
| 2008/0272199 A1 | 11/2008 | Kammer et al. |

* cited by examiner

MODULAR FLUID WARMER

CROSS-REFERENCE TO RELATED APPLICATION

Not applicable.

STATEMENT OF FEDERALLY SPONSORED RESEARCH OR DEVELOPMENT

Not applicable.

BACKGROUND OF THE INVENTION

This invention relates to the heating of a fluid disposed in a container. In particular, this invention relates devices and methods for the efficient heating of a fluid prior to its introduction into a body.

During medical care, it may be necessary to introduce a fluid into a human body intravenously. Such fluids may include, for example, blood, saline solution, antibiotic solution, and the like. Prior to administration, these fluids are usually stored in containers such as bags or bottles.

However, many of these fluid degrade at room temperature when outside of a body. Since the demand for many of these fluids is unpredictable (e.g., due to the nature of emergency conditions), it is preferable to maintain an inventory of many of these fluids within a hospital.

To prevent the degradation and to maintain the efficacy of such fluids, the fluids are conventionally refrigerated or frozen. Then, as needed, the fluids are warmed prior to their administration. In cases where large amounts of fluid are introduced to the body intravenously over a short period of time, it may be necessary to warm these fluids close to body temperature (around 98.6° F.) to prevent the patient from entering a hypothermic condition.

Conventionally, a hospital has an oven with a large capacity that heats the fluid containers prior to use. Usually, this oven is designed to have sufficient excess capacity to warm enough containers to satisfy the needs of the hospital in a worse case scenario. However, more frequently, only a fraction of the capacity of the oven is utilized. This under-utilization of the volume of the oven means that it may take longer to heat the entire volume up to the desired temperature and that energy is lost when the oven is at less than capacity.

Further, when a container is placed in the oven, it must be tagged or in some way monitored to ensure that the fluid does not stay in the oven too long and spoil. Particularly, when an oven warms multiple containers at once, there must be a system in place that determines the length of time that a particular container has been in the oven.

Hence, a need exists for an improved fluid warmer that more efficiently heats fluids prior to use in the body.

SUMMARY OF THE INVENTION

According to one aspect of the present invention, a modular fluid warmer is disclosed for heating a fluid disposed in a container to a desired temperature. The modular fluid warmer includes a shelf having a substantially horizontally extending support surface for supporting the container having the fluid disposed therein. A support structure supports the shelf and includes a back wall. A heating element is located proximate the support surface. A controller selectively operates the heating element to warm the container placed on the support surface. A first mating structure is formed on an upper surface of the back wall and a second mating structure is formed on a lower surface of the back wall. The first mating structure of the modular fluid warmer is configured to mate with a second mating structure of another modular fluid warmer to stack the modular fluid warmers.

According to another aspect of the present invention, a method of stacking a plurality of modular fluid warmers is disclosed. A back plate is provided that is sized to receive a number of modular fluid warmers, such that each of the modular fluid warmers are configured to heat a fluid disposed in a container. The modular fluid warmers are stacked by attaching each of the modular fluid warmers to the back plate and nesting a first mating structure of one of the modular fluid warmers into a second mating structure of another of the modular fluid warmers. The stacking of the modular fluid warmers by attachment to the back plate and nesting the modular fluid warmers into one another forms a stacked assembly.

Thus, the present invention provides a modular fluid warmer and a stacked assembly of modular fluid warmers that are can heat fluids more quickly and efficiently than existing fluid warmers. As the stacked assembly is modular, it is adjustable in capacity such that any number of units may be included when the assembly is formed. Further, as each of the modular fluid warmers can be independently operated, the energy used to heat the fluid is only directed to the shelves that are occupied. Moreover, the operation of each of the modular fluid warmers is simple, requiring only that the operator place the bag or bottle on the support surface to begin heating and, once the bag or bottle is heated, that the operator remove the bag or bottle to turn off the heating elements.

These and still other advantages of the invention will be apparent from the detailed description and drawings. What follows is merely a description of some preferred embodiments of the present invention. To assess the full scope of the invention the claims should be looked to as the preferred embodiments are not intended to be the only embodiments within the scope of the claims.

DETAILED DESCRIPTION OF THE PREFERRED EMBODIMENTS

Figure 1:
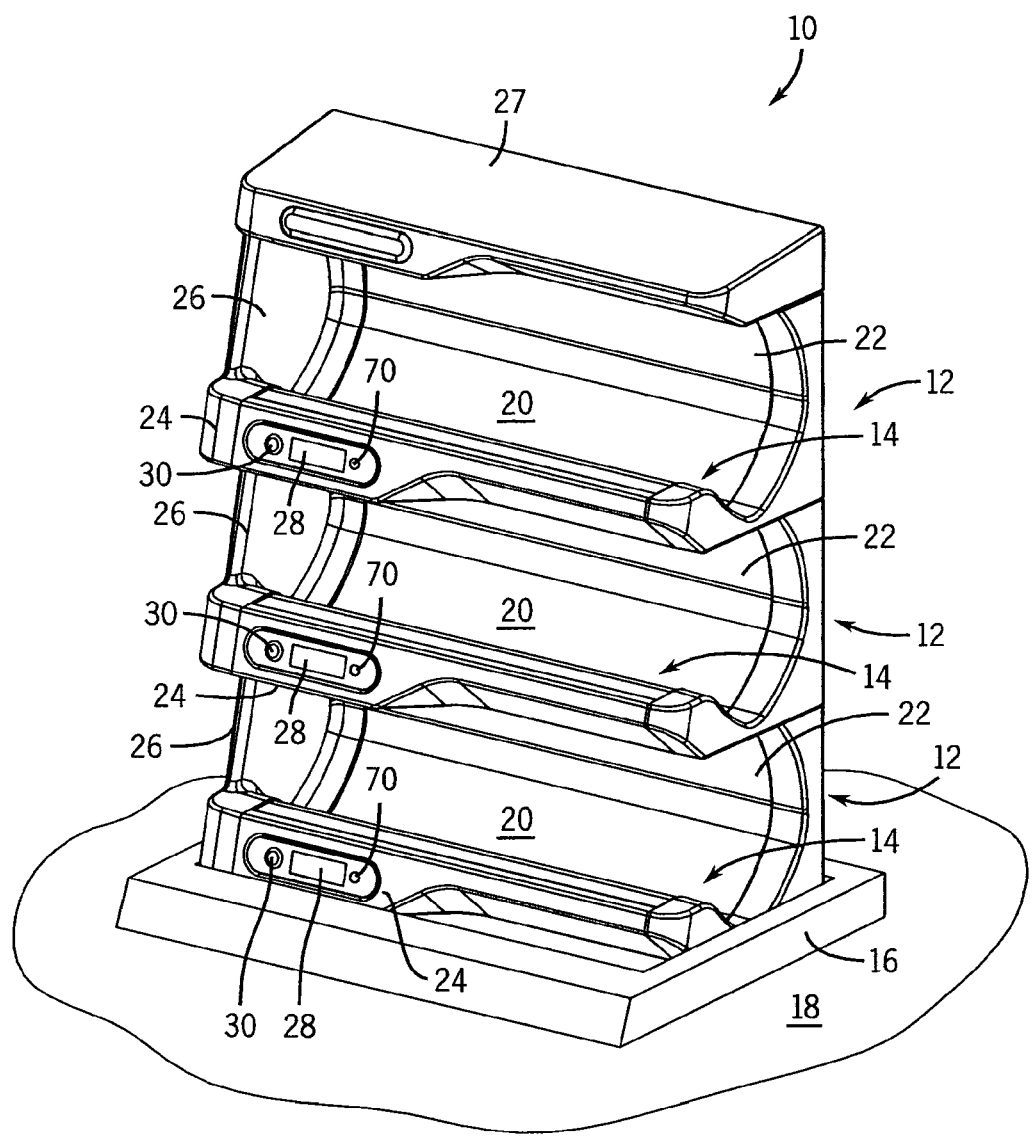
FIG. 1 is an environmental view of a stacked assembly of modular fluid warmers docked in a countertop pedestal.

Referring first to FIG. 1, a stacked assembly 10 is composed of a number of modular fluid warmers 12. As shown, the modular fluid warmers 12 are stacked three high, thus providing three shelves 14 for the placement of the containers. Although the stacked assembly 10 is shown as containing three modular fluid warmers 12, it should be appreciated that the stacked assembly 10 can include one or more modular fluid warmers 12. As shown in FIG. 1, the stacked assembly 10 is docked in a countertop pedestal 16 that rests on the surface of a table 18.

Each of the modular fluid warmers 12 form shelves 14 having support surfaces 20 for the placement of a container (not shown), such as a bag or bottle, that is filled with fluid. As can be seen best in FIG. 3, the support surface 20 is essentially C-shaped for receiving the bag or bottle. Although essentially C-shaped, the support surface 20 also has a portion that is flat with a bend so as to better receive bottles having a generally square-shaped cross-section or a relatively rigid flat surface. The support surface 20 is part of a support structure 22 which will be described in further detail below with respect to FIGS. 7 and 8. The support surface 20 is heated by a heating element 23 (best seen in FIGS. 3, 7, and 8), which is attached to the underside of the support surface 20.

The support structure 22 of each of the modular fluid warmers 12 is substantially surrounded by a casing 24. The casing 24 may be formed of a engineered plastic material that does not deform at room temperature to slightly above room temperature (50° F. to approximately 175° F.). On the left side of each of the modular fluid warmers 12, there is a side wall 26 that is integrally formed with the casing 24. On the top of the stacked assembly 10, a top casing 27 hangs over the top shelf.

At least one benefit of the modular fluid warmers 12 as shown, is that the shelves 14 provide easy access to the support surface 20 for the placement or the removal of a container. Thus, it is not necessary to open or close a door to load or remove a container from the support surface 20. Although a door could be present to form a compartment or chamber that retains heat, such a door is not deemed necessary in the present invention given the location of the heating elements and method of warming.

Each of the modular fluid warmers 12 have a display 28 with a recall button 30. This display 28 can be used display whether or not a container is sensed on the support surface 20, temperature information (e.g., the temperature of the container being heated), or time information (e.g., the time that the container being heated has been at the desired temperature). In one form, when the shelf 14 is empty, the display 28 will display four horizontal dashed lines. This indicates to a user that the modular fluid warmer 12 is operating and ready to receive a container. When the shelf 14 is occupied, the display 28 will show a scrolling vertical line to indicate that the bag or bottle has been sensed on the shelf 14. The recall button 30 may be depressed to indicate the time or the time at temperature. To achieve this functionality, there may be more than one recall button or depressing the recall button 30 may cause the display 28 to cycle through the available data (i.e., the first press of the recall button provides the temperature of the item, the second press provides the time at temperature, the third press indicates the detection status of an item, and so forth). Although one form of operational information recall has been disclosed, other ways of displaying and recalling information could also be employed.

Referring now to FIGS. 2A-2D and FIG. 3, a series of steps for assembling the stacked assembly 10 is shown. In general, the stacked assembly 10 is formed by attaching individual modular fluid warmers 12 to a back plate 32 that is sized to receive the desired number of modular fluid warmers 12. In this particular assembly, the stacked assembly 10 is only two modular fluid warmers high. However, as stated above, the back plate 32 could be sized to receive any number of modular fluid warmers 12.

The back plate 32 will now be described in detail. The back plate 32 includes a back wall 34 having two side walls 36 and a top wall 38 extending forward therefrom. The two side walls 36 and the top wall 38 also meet along edges to form a top of the stacked assembly 10. On one of the side walls 36, near the top of the back plate 32, there is a power switch 40 which will be used to toggle power to all of the modular fluid warmers 12 that are attached to the back plate 32. The back wall 34 includes sets of tabs 42 that extend forward and upward for receiving the modular fluid warmers 12. The back wall 34 contains a number of other apertures including screw holes 44 for securing screws through the back plate 32 and into the modular fluid warmers 12 and mounting holes 46 for securing the stacked assembly 10 to a wall or the like.

Figure 3:
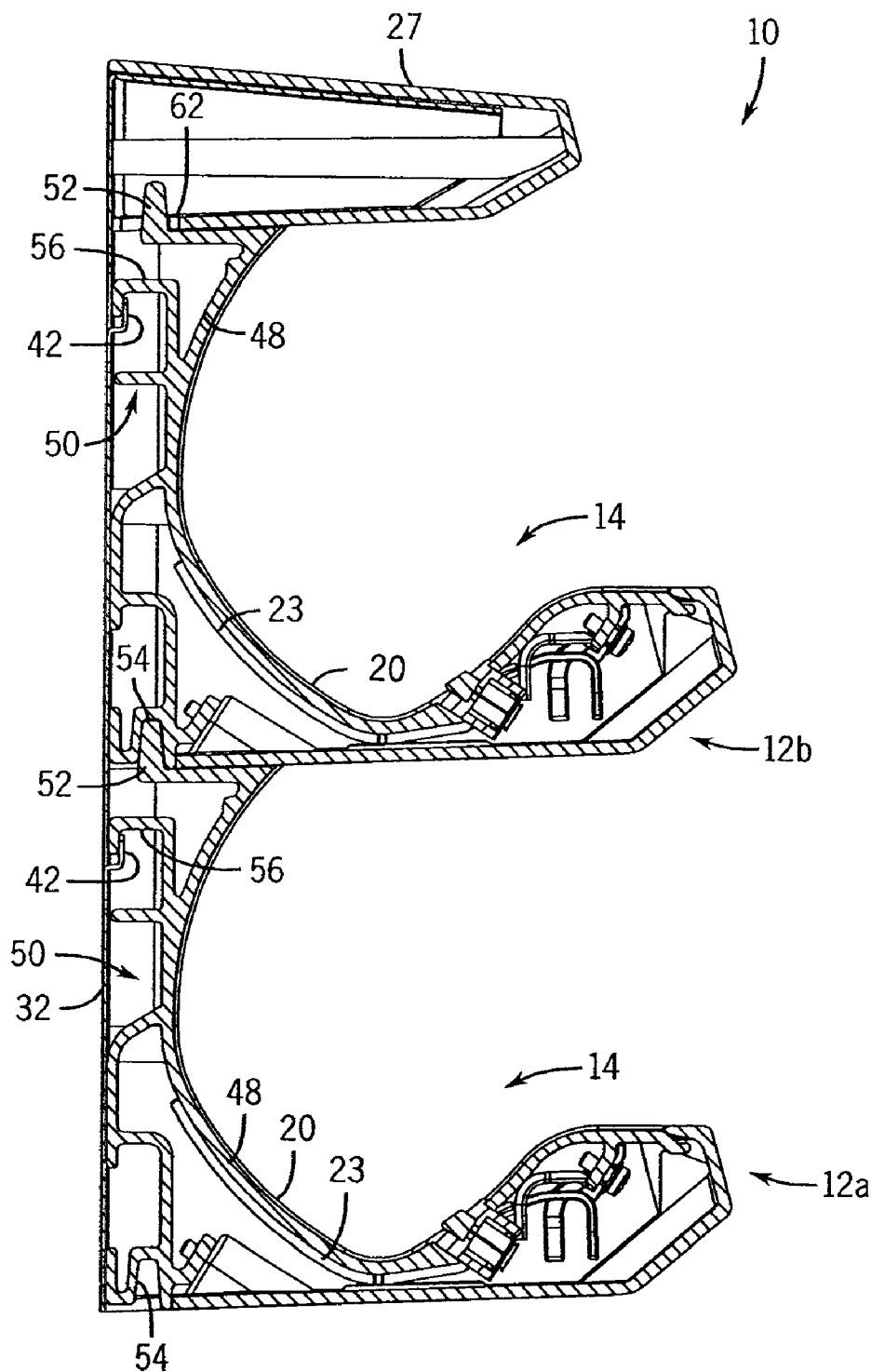
FIG. 3 is a cross sectional view of the stacked assembly of FIG. 2D.

As best seen in FIG. 3, each of the modular fluid warmers 12 include a support structure 22. The support structure 22 includes an essentially C-shaped portion 48 which serves as the support surface 20 and shelf for receiving the container to be heated. The support structure 22 further includes a back wall portion 50 that supports the shelf and includes many features required to form the stacked assembly 10. In the form shown in FIGS. 7 and 8, the portions 48 and 50 are integrally formed.

On the upper surface of the back wall portion 50, a first mating structure 52 is provided in the form of a tongue. On the lower surface of the back wall portion 50, a second mating structure 54 is provided in the form of a groove that is shaped to receive the tongue. Between the top and bottom surfaces of the back wall portion 50, a tab 56 extends out and down from the back wall portion 50. This tab 56 is formed to be slid over the set of tabs 42 formed in the back plate 32. Also a number of screw holes 58 are formed on the back side of the back wall portion 50 for use during attachment of the modular fluid warmer 12 to the back plate 32.

Given the complex profile of the support structure 22, it may be formed by an extrusion process and is composed of, at least in one form, aluminum or an aluminum alloy. Although the support structure 22 is shown as being a integrally-formed component, the support structure 22 could also be formed by the attachment of two or more separate components that provide features similar to the integrally formed component.

Figure 2A:
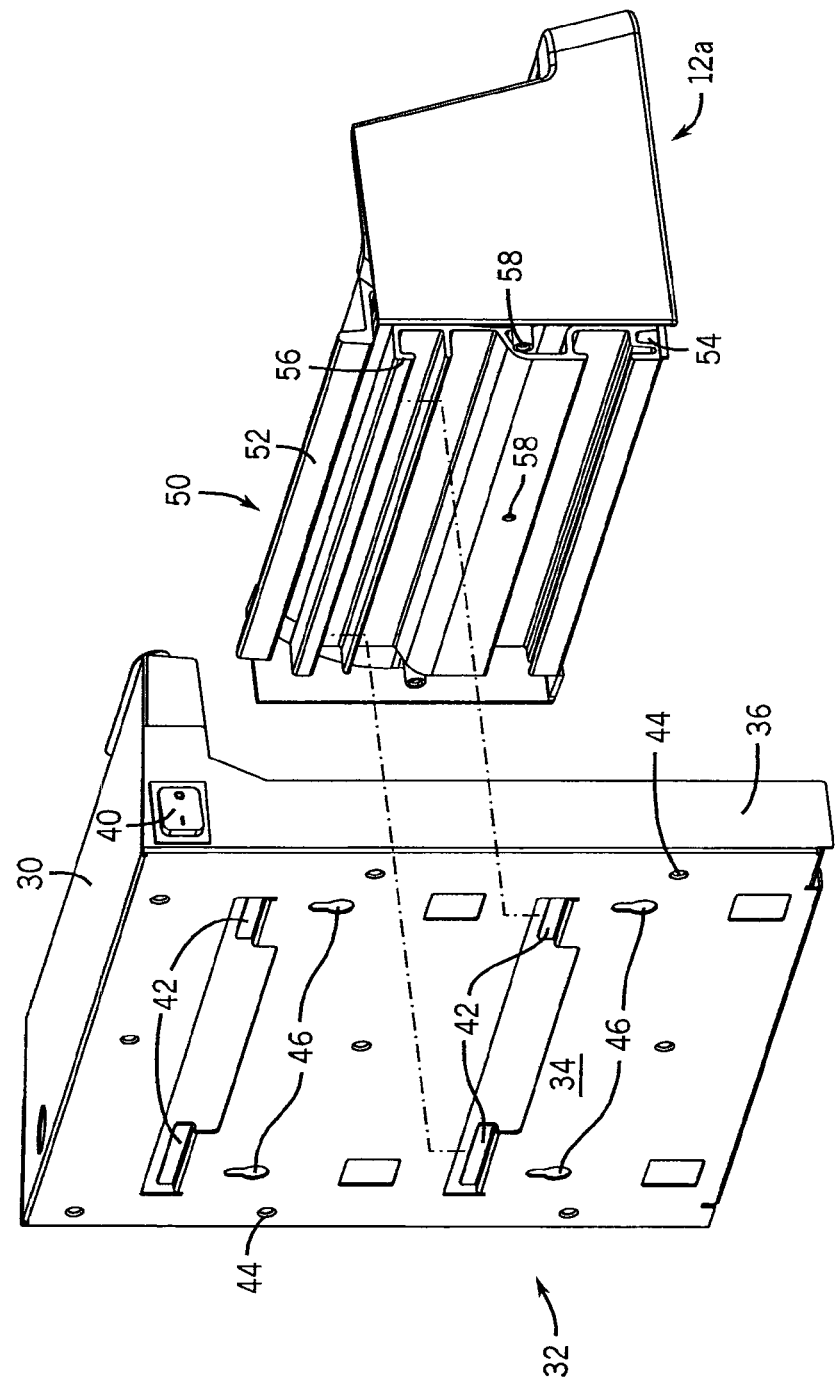
FIGS. 2A-2D are perspective views of the steps used to assemble a stacked assembly having two modular fluid warmers.

Looking first at FIG. 2A, a first modular fluid warmer 12a is attached to the lowest available reception spot on the back plate 32 by attaching the back wall portion 50 of the modular fluid warmer 12a to the back plate 32. The tab 56 of the back wall 34 of the support structure 22 is slid over and down on the set of tabs 42 on the back plate 32. When the tabs 42 and 56 engage one another, then a set of screw holes 58 on the backside of the support structure 22 align with the set of screw holes 44 on the back plate 32. Screws are then threaded through the screw holes 44 and 58 to attach the first modular fluid warmer 12a to the back plate 32. Although not shown, it is contemplated that the second mating structure 54 could engage a mating structure formed proximate the bottom of the back plate 32 to further secure the first modular fluid warmer 12a to the back plate 32.

Figure 2B:
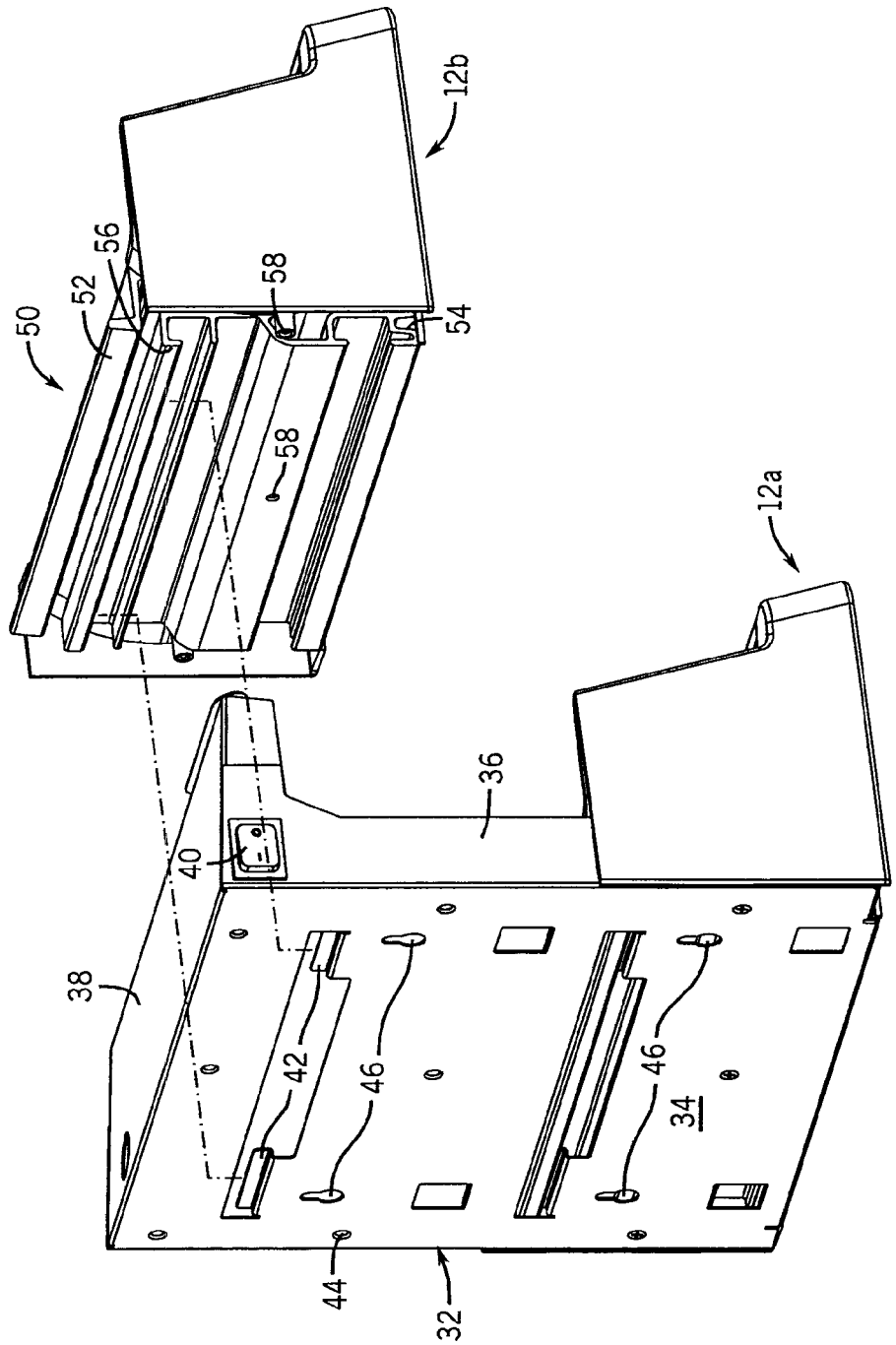

Looking now at FIG. 2B, a second modular fluid warmer 12b is shown being attached to the back plate 32 above the first modular fluid warmer 12a. The second modular fluid warmer 12b is attached to the back plate 32 in a similar fashion as the first modular fluid warmer 12a. Again, the tab 56 of the back wall portion 50 of the second modular fluid warmer 12b is attached to a set of tabs 42 on the back plate 32. Notably, as the second modular fluid warmer 12b is slid back and over the set of tabs 42, there is no interference issue between the portion of the side wall 36 of the back plate 32 and the casing 24 of the second modular fluid warmer 12b because the second modular fluid warmer 12b has a U-shaped section proximate the ends that provides clearance for the insertion. Once the second modular fluid warmer 12b is positioned on the back plate 32, the second modular fluid warmer 12b may also be secured to the back plate 32 using screws.

As best shown in FIG. 3, as the second modular fluid warmer 12b is slid down into place, the second mating structure 54 on the bottom surface of the second modular fluid warmer 12b interfits with the first mating structure 52 on the top surface of the first modular fluid warmer 12a. In the particular form shown, the groove of the second modular fluid warmer 12b is slid over the tongue of the first modular fluid warmer 12a. Although a tongue and groove connection is shown, the mating have could take on a number of different forms. In some forms, these connections may snap or lock the two modular fluid warmers together.

It is contemplated that each of the fluid warmers will receive electrical power from a power source operated by the power switch 40. Groups of wires running from the power source to each of the modular fluid warmers 12a and 12b supply power to each of the modular fluid warmers 12a and 12b. The wires may be connected to each of the modular fluid warmers 12 and 12b using either a screw terminal or a plug-type connection. It is contemplated that the modular fluid connectors could be electrically connected in either parallel or series. For ease of assembly and for improved troubleshooting if an individual modular fluid warmer fails, parallel connections may be preferable.

Further, as the modular fluid warmers 12a and 12b are stacked onto one another, they could have electrical connections that allows each of the modular fluid warmers 12a and 12b to receive power from the same power source in series or parallel.

Figure 2C:
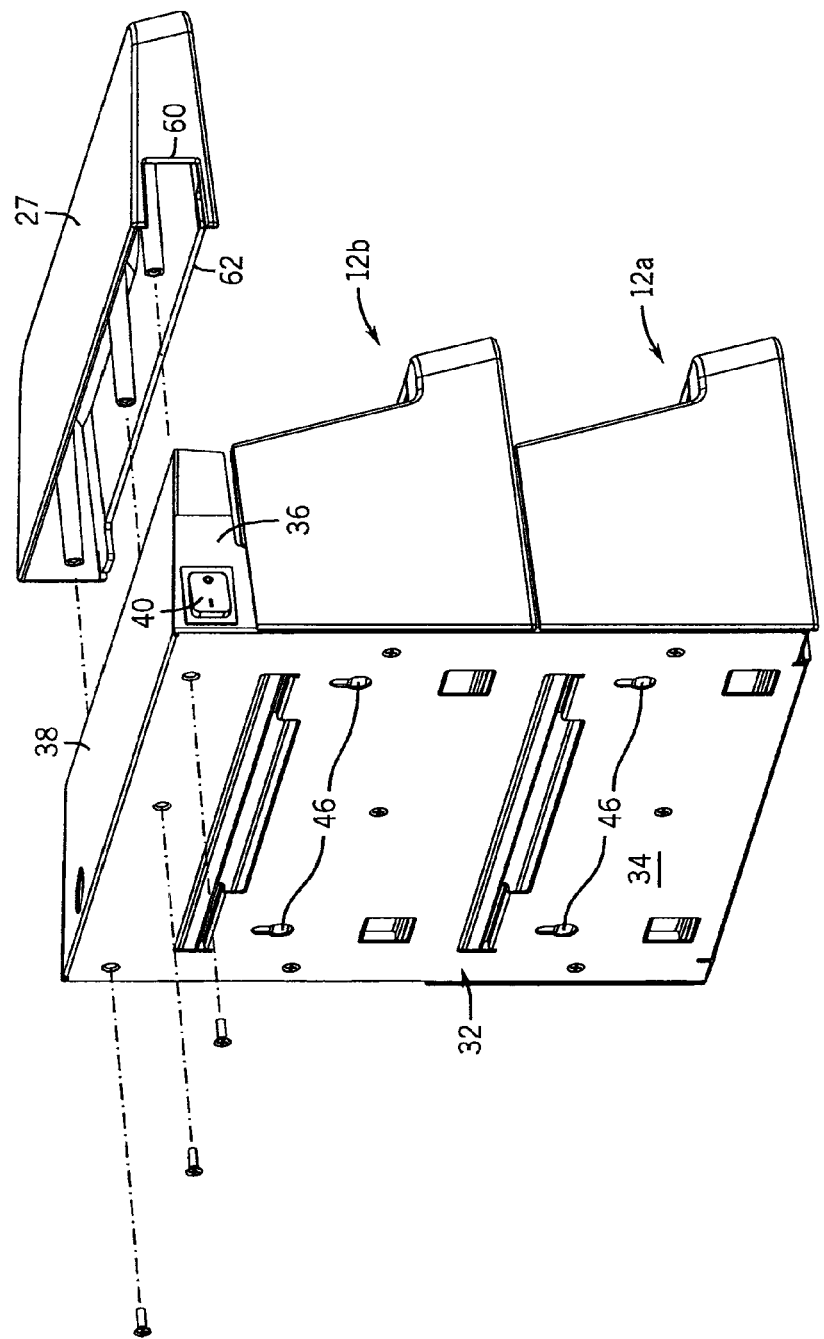
Figure 2D:
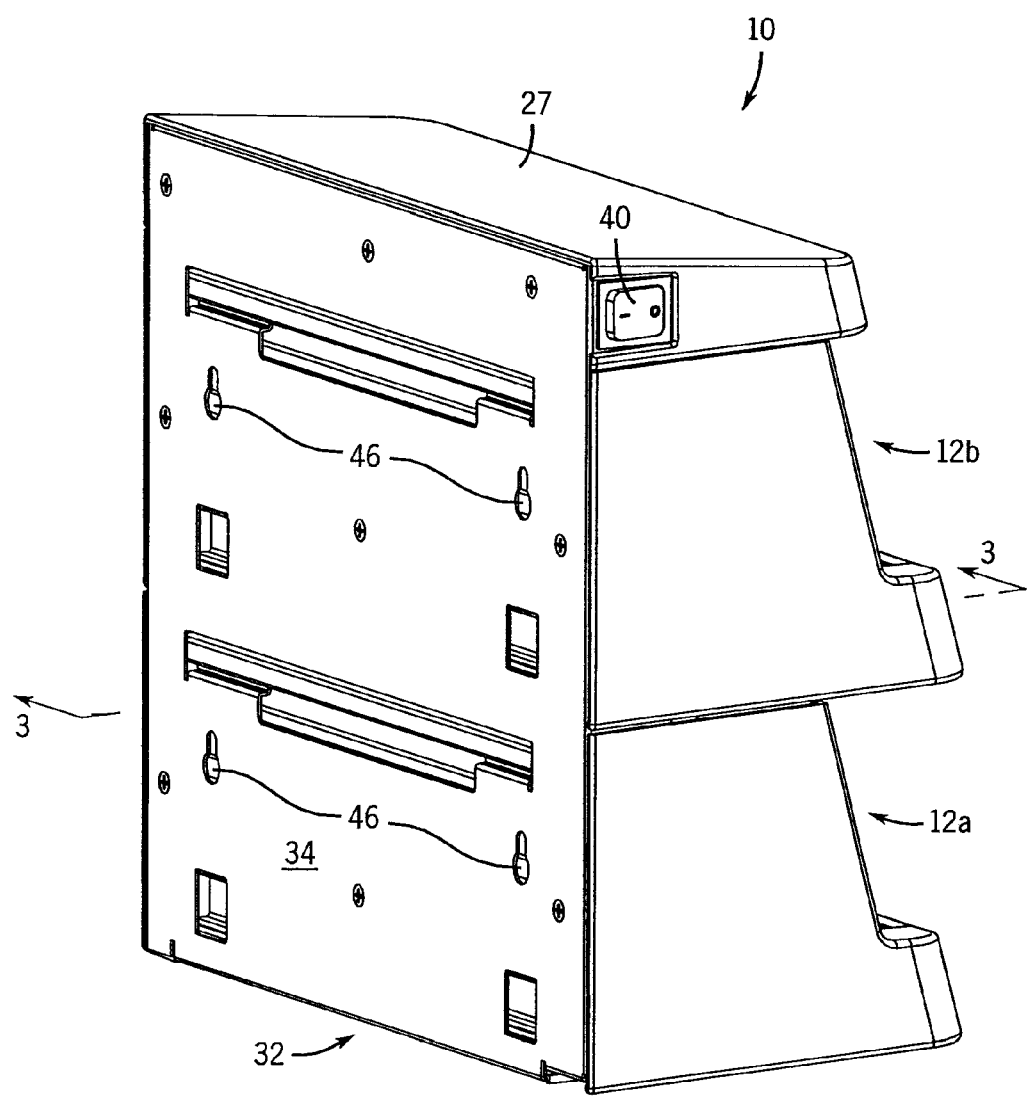

As shown in FIGS. 2C and 2D, once both of the modular fluid warmers 12a and 12b are attached to the back plate 32, the top casing 27 may be slid over the overhanging section of the back plate 32. This top casing 27 may match the outer appearance of the casing 24 of the modular fluid warmers 12a and 12b and could be used to brand the stacked assembly 10. The top casing 27 has a cutout 60 for wrapping around the power switch 40 and a bottom edge 62 that is formed to terminate prior to contacting the first mating structure 52 of the second modular fluid warmer 12b. It is contemplated that in some forms of the invention, the modular fluid warmers 12a and 12b themselves might be freely hung on the back plate 32 without screws and it is only the top casing 27, once secured to the back plate 32 with screws, that permanently retains the modular fluid warmers 12a and 12b on the back plate 32.

Although the modular fluid warmers 12a and 12b have been shown as being attached one at a time to the back plate 32, it is contemplated that the modular fluid warmers 12a and 12b could be pre-stacked and then attached to the back plate 32 as a group.

Further, although the back plate 32 has been shown as a single plate sized to accommodate a specific number of modular fluid warmers, it is contemplated that the back plate 32 may be composed of a number of plates attachable to one another. In this way, if it was desirable to increase the capacity of the stacked assembly 10, another modular fluid warmer could be easily added.

Figure 4:
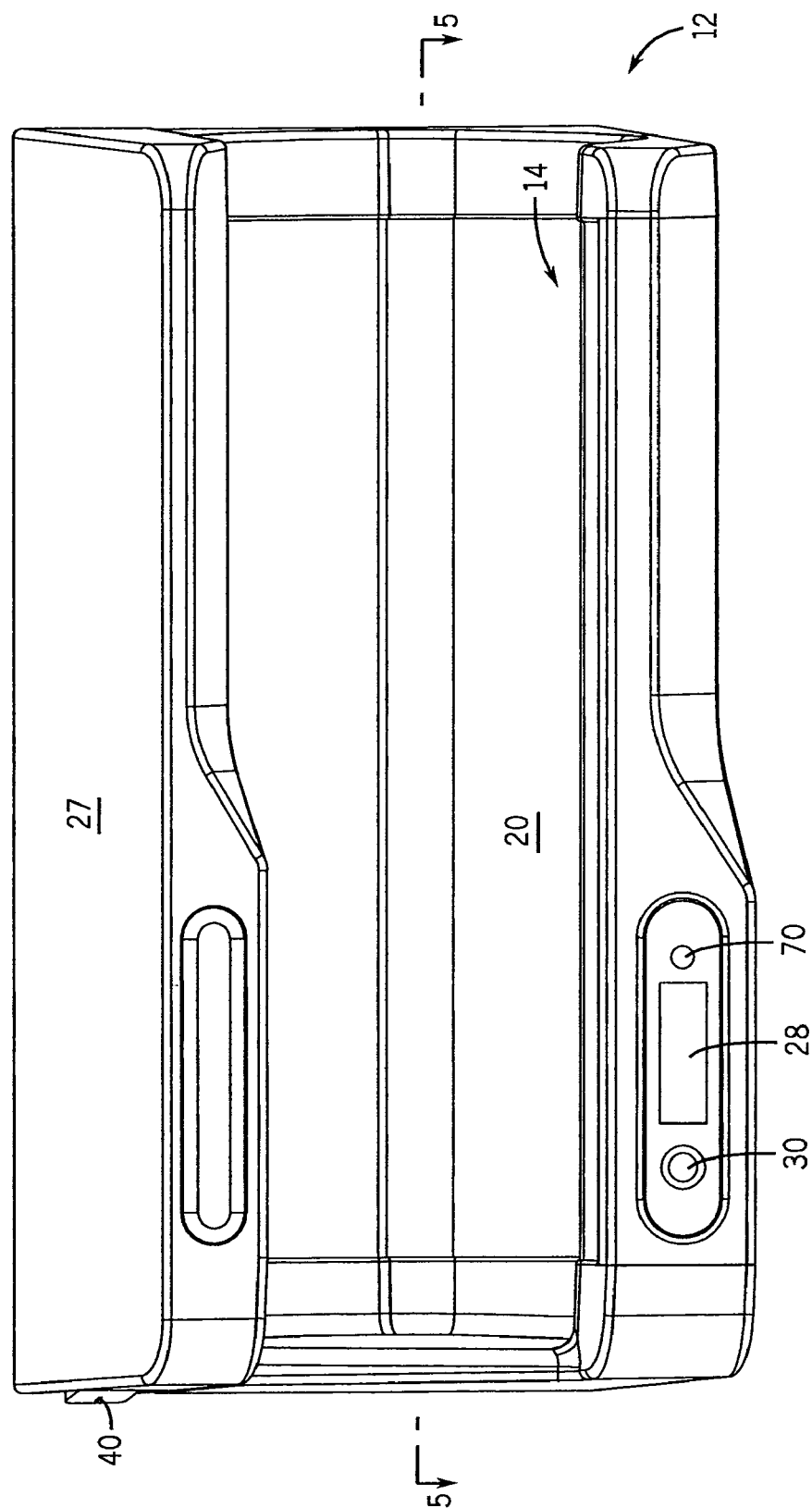
FIG. 4 is a front plan view of a modular fluid warmer.
Figure 5:
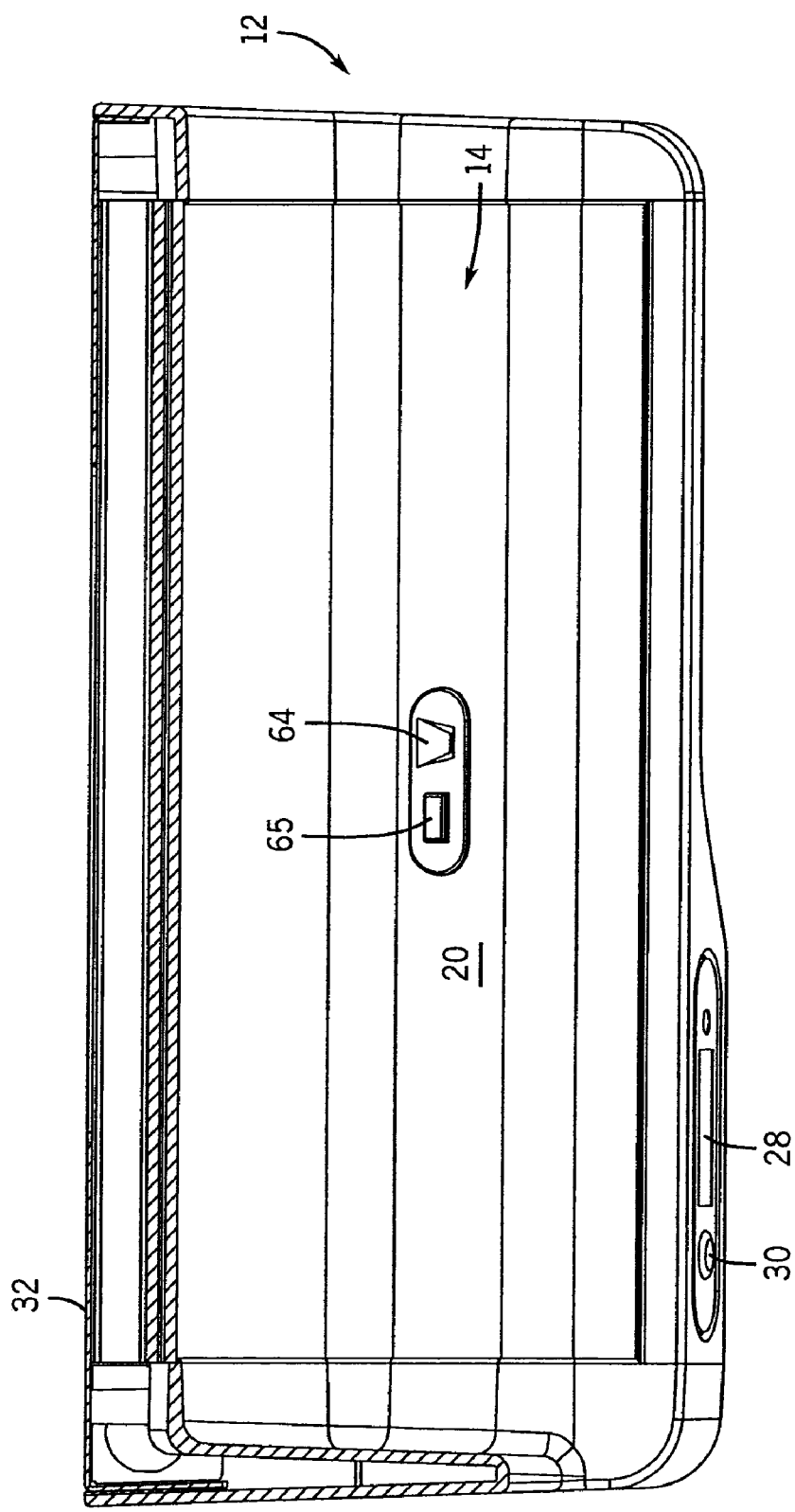
FIG. 5 is a cross sectional view of the modular fluid warmer along a line 5-5 showing an optical sensor and an item temperature sensor on the support surface.
Figure 6:
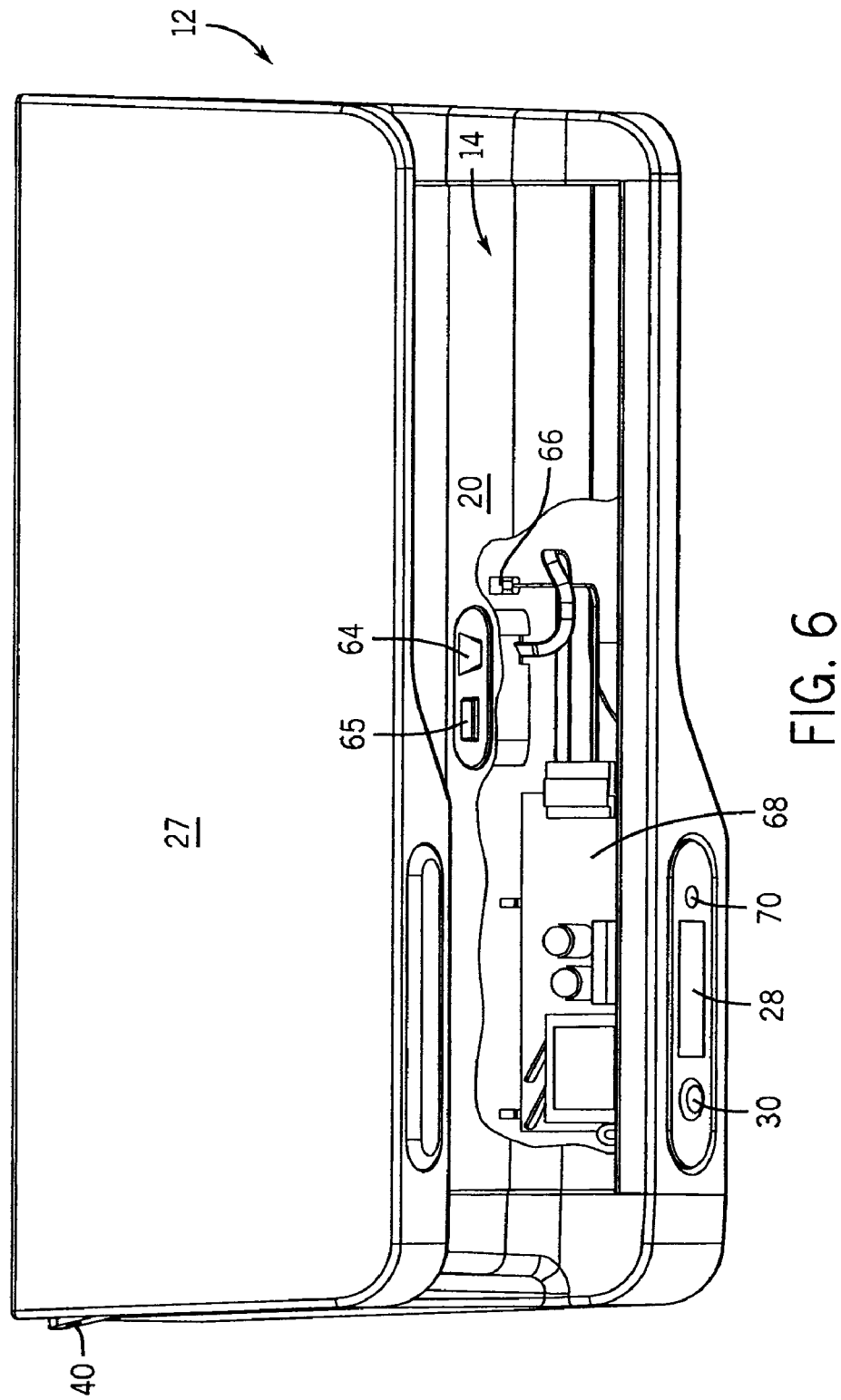
FIG. 6 is a cutaway view of the support surface of the modular fluid warmer to reveal the controller and wiring for various sensors.

Referring now to FIGS. 4-6, the sensors found on the support surface 20 can be seen. In particular, an optical item sensor 64 for detecting the presence of a container or item and an item temperature sensor 65 for measuring the temperature of the item received on the support surface 20 can be seen. As best seen in FIG. 6, there is also a heating element temperature sensor 66 for measuring the temperature of the heating element 23. All of these sensors are wired to the controller 68 which is located proximate the display 28.

In operation, when a container is received on the support surface 20, the optical item sensor 64 detects the container. When the optical item sensor 64 detects the container, the controller 68 starts the heating element 23 to heat the support surface 20. As the heating element 23 warms the support surface 20, the controller 68 continually reads the temperature of the container being heated using the item temperature sensor 65 and the heating element 23 using the heating element temperature sensor 66. Once the temperature of the container is within an appropriate temperature range for administration, then a timer in the controller 68 may start recording time to determine the length of time at which the container is maintained at the set point temperature of the modular fluid warmer 12. When the temperature of the container (and fluid therein) is within acceptable range for use, an LED light 70 on the front of the modular fluid warmer 12 may illuminate to indicate that the fluid is ready for administration. This indication could also be provided using the display 28.

Measuring time at temperature is generally preferable over measuring residence time, as the rate of degradation of the fluid is more closely related to the length of time at peak thermal temperatures than the total length of time in the modular fluid warmer 12. However, it is contemplated that the timer in the controller 68 could be configured to measure other time quantities, such as residence time or the like.

When the warmed container is removed from the support surface 20, the optical item sensor 54 detects that there is no longer an item on the support surface 20. This information is sent to the controller 69, which turns off the heating element 23 and resets any running timer. The modular fluid warmer 12 sits idle until another container is detected which restarts the heating element 23 and any other associated timing cycle.

As each of the modular fluid warmers 12 operate independently of one another, only the units in the stacked assembly 10 that are occupied by an item or container are heated. This provides flexibility in capacity and only requires the energy necessary to heat the occupied modular fluid warmers. Thus, the present invention provides efficient and selective warming of containers with little user interaction other than adding and removing the container from the support surface 20.

Figure 7:
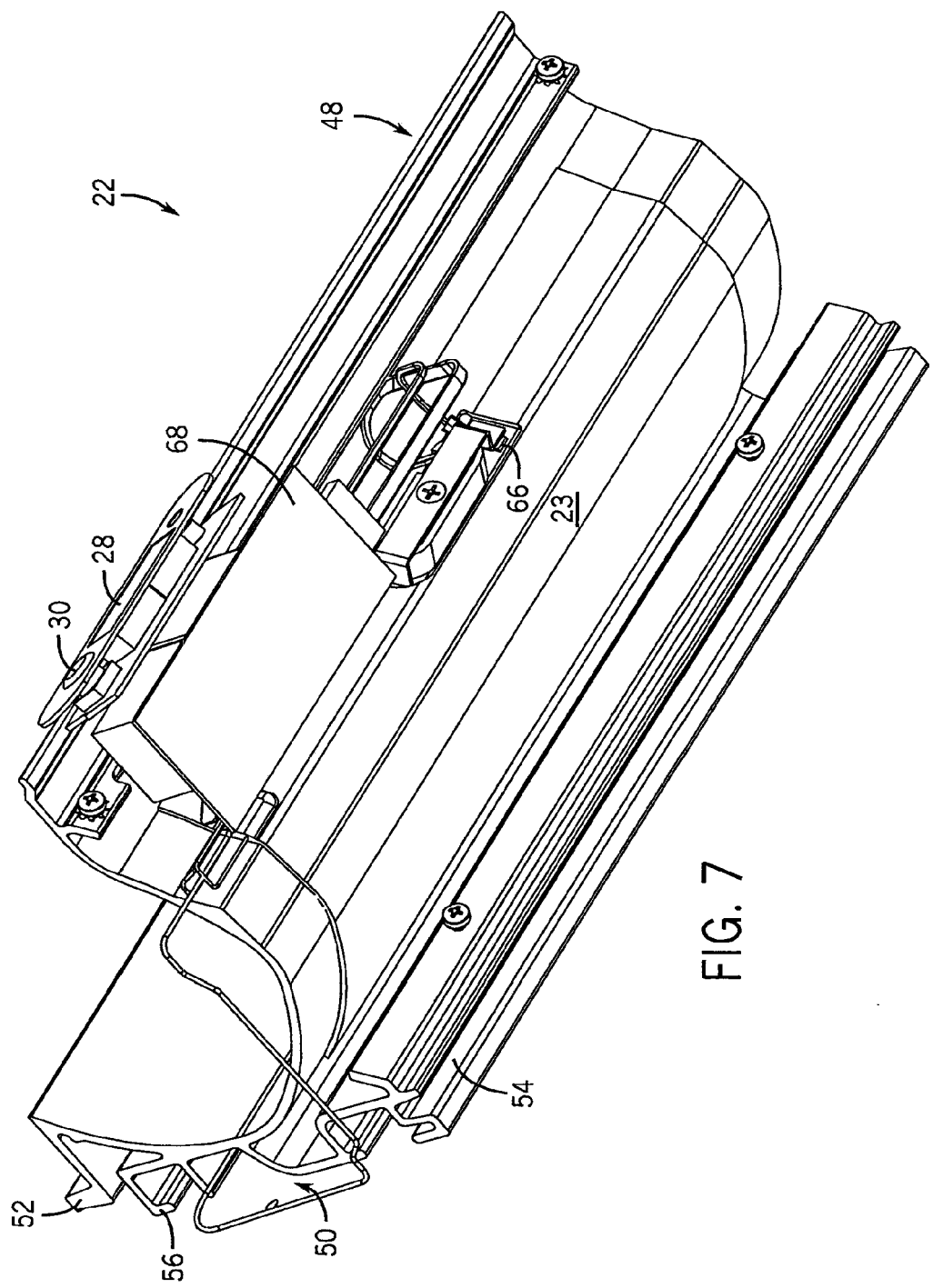
FIG. 7 is a front bottom perspective view of the modular fluid warmer with the plastic case removed to show the heating element on the underside of the support surface.
Figure 8:
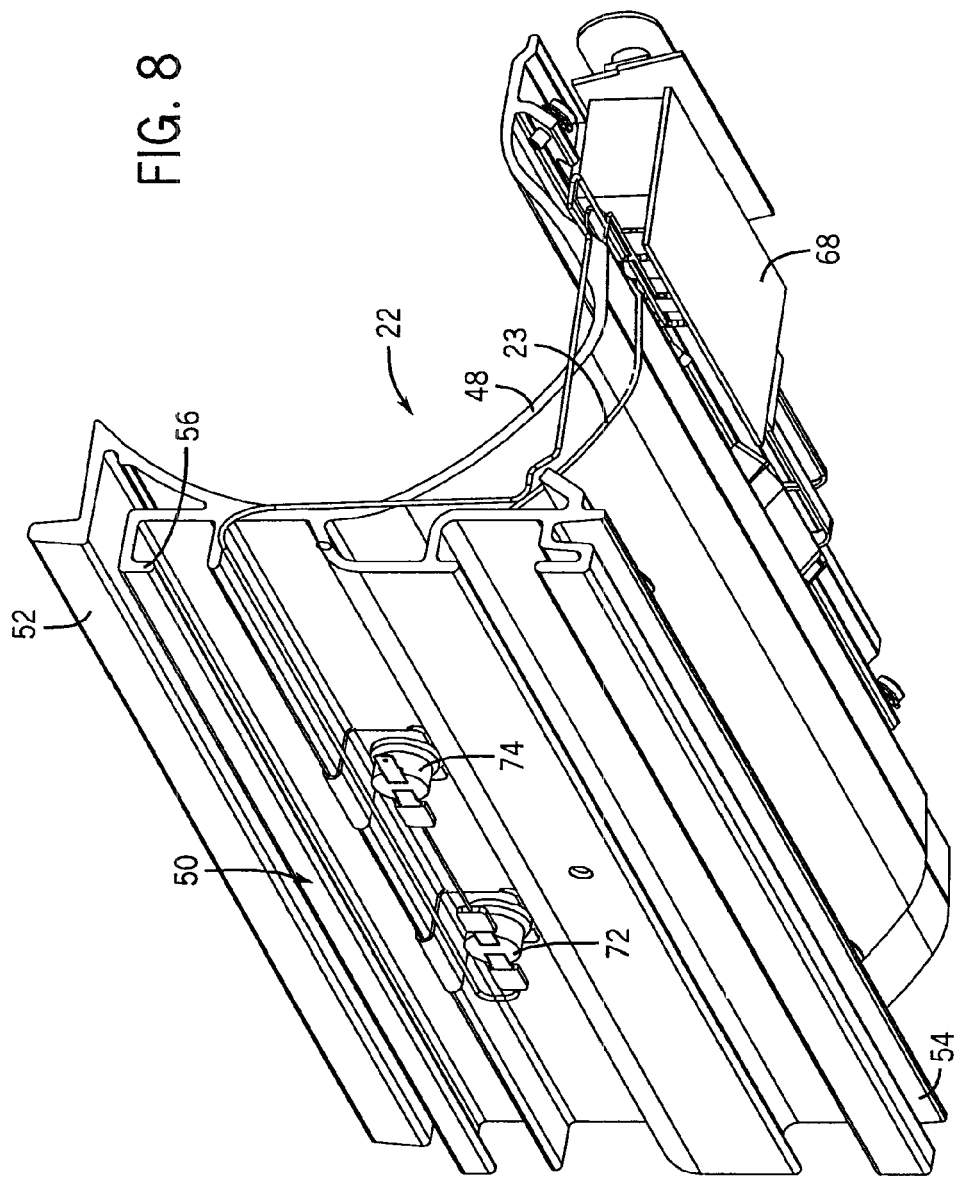
FIG. 8 is a rear bottom perspective view of the modular fluid warmer as in FIG. 7 showing the over temperature sensors on the back wall of the support structure.

Referring now to FIGS. 7 and 8, the support structure 22 is shown in more detail. As previously described, the support structure 22 includes the essentially C-shaped portion 48 and the back wall portion 50.

The support structure 22 may be comprised of aluminum and may be formed using an extrusion process. Although the support structure 22 may be formed of other materials, by other processes, or by joining separately formed components, using an aluminum extrusion process allows for an integrally formed support structure that can have complex features in cross section, such as the mating structures 52 and 54 and the tab 56.

FIGS. 7 and 8 most clearly show the heating element 23 wrapping around the underside of the essentially C-shaped portion 48 proximate the support surface 20. This heating element 23 may be a resistive heating element such as a silicon pad. However, other resistive materials or other types of heating elements could also be employed.

Referring specifically to FIG. 8, two support surface temperature sensors 72 and 74 are mounted on the back wall portion 50 of the support structure 22 proximate the support surface 20. These support surface temperature sensors 72 and 74 measure a temperature of the support structure 22 to ensure that the heating element 23 has not overheated. There is some redundancy built into the number of sensors, such that if one of the sensors fails, there is at least one backup temperature sensor that will detect a faulty condition.

Figure 9:
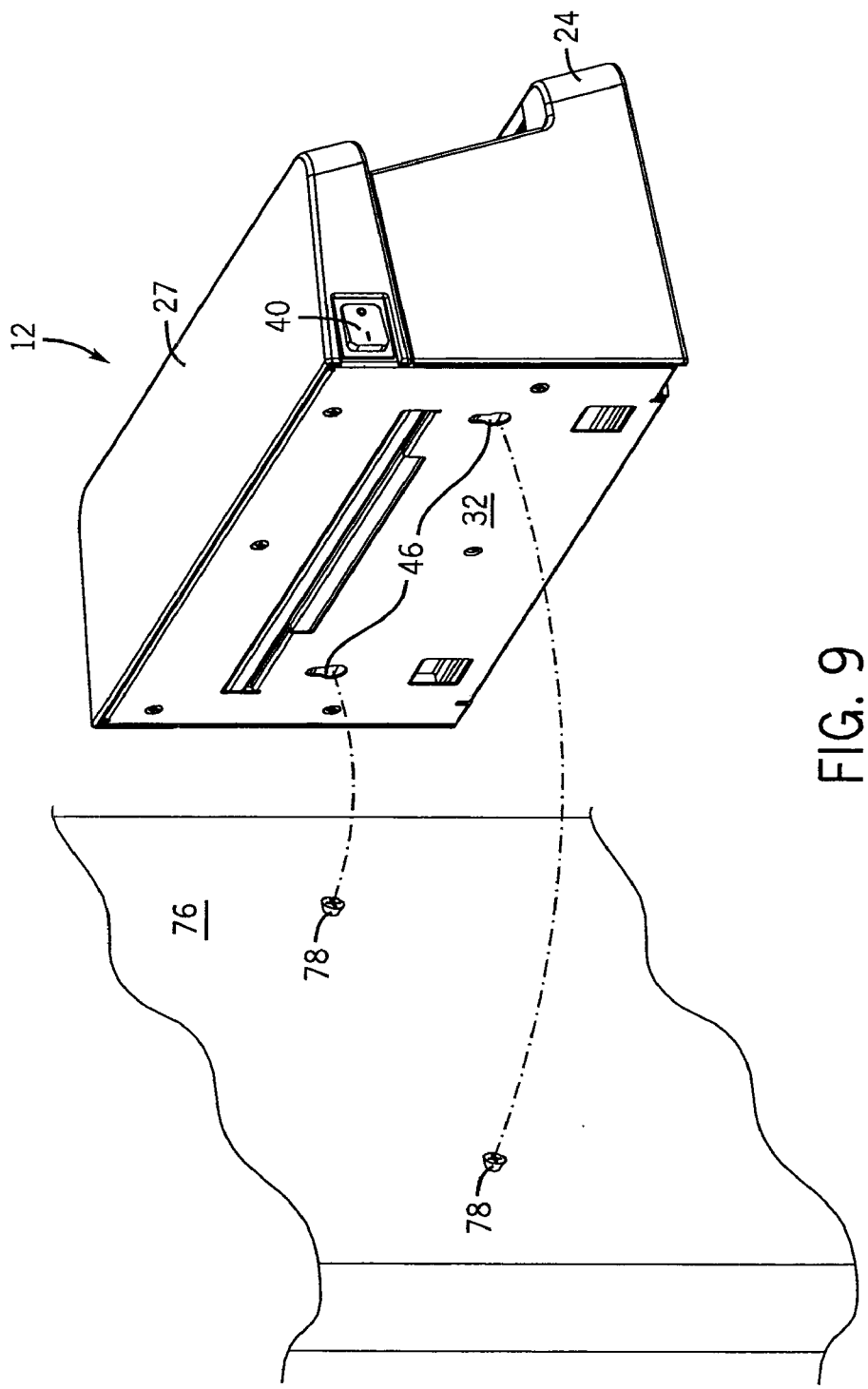
FIG. 9 is an environmental view of the modular fluid warmer being attached to a wall.
Figure 10:
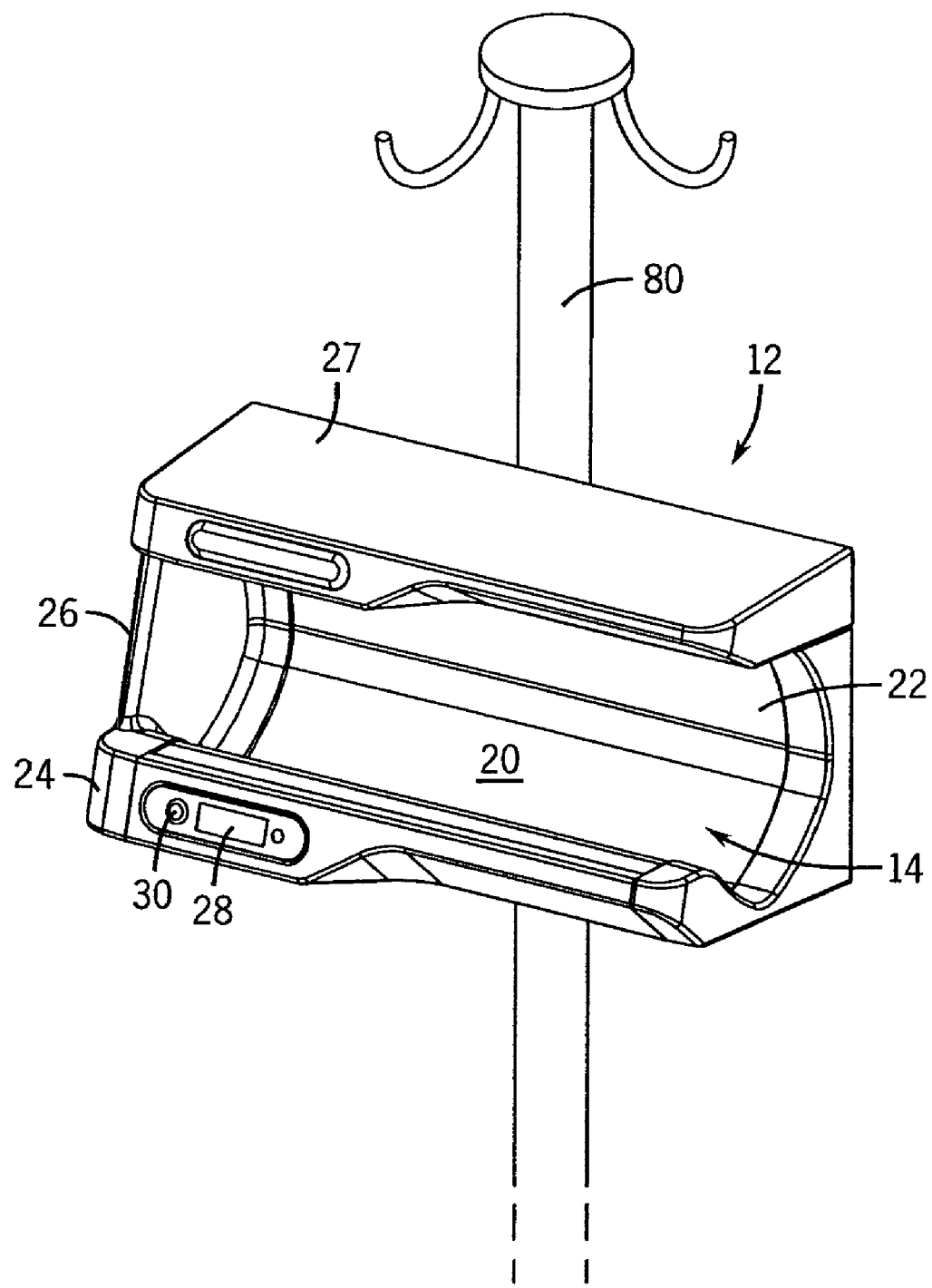
FIG. 10 is an environmental view of the modular fluid warmer attached to a moveable I.V. pole.

FIGS. 9 and 10 show some of the different ways in which the stacked assembly 10 can be supported other than sitting on a surface.

Referring now to FIG. 9, a modular fluid warmer 12 is shown being mounted to a wall 76. The wall 76 has two screws 78 screwed part way into the wall 76. The mounting holes 46 in the back plate 32 of the modular fluid warmer 12 are pushed over the screws 78 and the modular fluid warmer 12 can be dropped into place to hang the modular fluid warmer 12 from the wall 76.

Referring now to FIG. 10, a modular fluid warmer 12 is shown attached to an I.V. pole 80. This I.V. pole 80 may include a number of caster wheels (not shown) at the base of the I.V. pole 80 so that the I.V. pole 80 can be transported. Attachment of the modular fluid warmer 12 to the I.V. pole 80 could be established in any one of a number of ways well known to those skilled in the art including hanging the modular fluid warmer 12 from a projection off of the I.V. pole 80, clamping the modular fluid warmer 12 using a collar to the I.V. pole 80, or the like.

It should be appreciated that while only a single fluid warmer has been shown as being mounted or attached to a wall or IV pole in FIGS. 9 and 10, that a stacked assembly 10 could likewise be attached in the same way. However, as the stacked assembly 10 has a back plate that is sized to match the number of shelves 14 in the stacked assembly 10, there may be more than one set of screws or the like to attach the stacked assembly 10 to the wall 76 or the I.V. pole 80.

Thus, the present invention provides a modular fluid warmer that, because of the intelligence of its control mechanism, presents many efficiencies. The modular fluid warmer is efficient in that it only operates when the compartment is occupied. Further, the modular fluid warmer only heats the occupied units, eliminating the heating of unused capacity. The device is time efficient in that it brings the bag or bottle up to temperature at the greatest possible rate without overheating. Additionally, the modular fluid warmer is labor efficient in that require little user interaction other than the placement of the bag or bottle into the device and the removal of the bag or bottle from the device when it is warmed.

Further, as the present invention is modular, it provides flexibility in capacity. Any number of modular fluid warmers can be combined to create a stacked assembly of desired capacity.

It should be appreciated that various other modifications and variations to the preferred embodiments can be made within the spirit and scope of the invention. Therefore, the invention should not be limited to the described embodiments. To ascertain the full scope of the invention, the following claims should be referenced.

What is claimed is:

1. A modular fluid warmer for heating a fluid disposed in a container to a desired temperature, the modular fluid warmer comprising:
    a shelf having a substantially horizontally extending support surface for supporting the container having said fluid disposed therein;
    a support structure supporting said shelf and including a back wall;
    a heating element proximate the support surface;
    a controller that selectively operates the heating element to warm the container placed on the support surface;
    a first mating structure formed on an upper surface of said back wall;
    a second mating structure formed on a lower surface of said back wall;
    wherein the first mating structure of the modular fluid warmer is configured to mate with a second mating structure of another modular fluid warmer to stack the modular fluid warmers;
    wherein the back wall of the support structure is attached to a back plate that is sized to receive the at least one modular fluid warmer; and
    wherein the back plate includes a power source having a plurality of wires for connecting to each of the at least one modular fluid warmer to provide power the at least one modular fluid warmer.

2. The modular fluid warmer of claim 1, wherein said support surface for receiving the item to be heated is essentially C-shaped.

3. The modular fluid warmer of claim 2, wherein the support structure is an extruded piece of aluminum.

4. The modular fluid warmer of claim 1, wherein the item is at least one of a bag and a bottle containing intravenous fluid.

5. The modular fluid warmer of claim 1, wherein the heating element is composed of a resistive material.

6. The modular fluid warmer of claim 5, wherein the resistive material includes silicon.

7. The modular fluid warmer of claim 1, further comprising an optical sensor to detect placement of an item on the support surface, the optical sensor signaling to the controller that the support surface is occupied.

8. The modular fluid warmer of claim 1, further comprising an item temperature sensor extending from the support surface for measuring a temperature of the item being heated, the item temperature sensor being connected to the controller.

9. The modular fluid warmer of claim 1, further comprising a heating element temperature sensor that measures a temperature of the heating element, the heating element temperature sensor being connected to the controller.

10. The modular fluid warmer of claim 1, further comprising a support surface temperature sensor that measures a temperature of the support surface, the support surface temperature sensor being connected to the controller.

11. The modular fluid warmer of claim 1, wherein the modular fluid warmer is attached to a wall.

12. The modular fluid warmer of claim 1, wherein the modular fluid warmer is attached to a mobile pole assembly.

13. The modular fluid warmer of claim 1, wherein the modular fluid warmer sits on a horizontal surface.

14. The modular fluid warmer of claim 13, wherein the modular fluid warmer docks in a countertop pedestal.

15. The modular fluid warmer of claim 1, wherein the controller further includes a timer for measuring a time at temperature for the item being heated.

16. The modular fluid warmer of claim 15, further comprising a display and a recall button, such that, when the recall button is pressed, the display indicates at least one of a temperature and time at temperature of the item being heated and, when the recall button is not pressed, the display indicates whether the item is received on the support surface.

17. A method of stacking a plurality of modular fluid warmers comprising:
    providing a back plate sized to receive a number of modular fluid warmers, each of the modular fluid warmers configured to heat a fluid disposed in a container;

stacking the modular fluid warmers by attaching each of the modular fluid warmers to the back plate and nesting a first mating structure of one of the modular fluid warmers into a second mating structure of another of the modular fluid warmers; and wherein the stacking of modular fluid warmers by attachment to the back plate and nesting the modular fluid warmers into one another forms a stacked assembly.

18. The method of claim 17, further comprising adding a top portion to the stack of fluid warmers, the top portion including a power switch that turns a power to the stacked assembly on and off.

19. A transportable fluid warmer assembly comprising:

a stacked assembly including a plurality of modular fluid warmers, each of the plurality of modular fluid warmers for heating a fluid disposed in a container to a desired temperature, each of the plurality of modular fluid warmers including:

a shelf having a substantially horizontally extending support surface for supporting the container having said fluid disposed therein;

a support structure supporting said shelf and including a back wall;

a heating element proximate the support surface;

a controller that selectively operates the heating element to warm the container placed on the support surface;

a first mating structure formed on an upper surface of said back wall; and a second mating structure formed on a lower surface of said back wall;

wherein the first mating structure of each modular fluid warmer is configured to mate with a second mating structure of another modular fluid warmer to stack the plurality of modular fluid warmers; and an I.V. pole having the stacked assembly attached thereto.

20. The transportable fluid warmer assembly of claim 19, wherein the I.V. pole supports the stacked assembly.

* * * * *